United States Patent
Kiesewetter et al.

(10) Patent No.: US 6,770,455 B1
(45) Date of Patent: Aug. 3, 2004

(54) METAL-CONTAINING RIBONUCLEOTIDE POLYPEPTIDES

(75) Inventors: Stefan Kiesewetter, Osterfeldern (DE); Eckehard Kuhn, Frickenhausen (DE); Bridgitte Koch-Pelster, Backnang (DE); Herwig Brunner, Stuttgart (DE)

(73) Assignee: Fraunhofer_Gesellschaft zur Forderung der Angewandten Forschung E.V., Munich (DE)

( * ) Notice: Subject to any disclaimer, the term of this patent is extended or adjusted under 35 U.S.C. 154(b) by 0 days.

(21) Appl. No.: 09/646,651

(22) PCT Filed: Nov. 30, 1998

(86) PCT No.: PCT/EP98/07722

§ 371 (c)(1),
(2), (4) Date: Jan. 16, 2001

(87) PCT Pub. No.: WO99/47561

PCT Pub. Date: Sep. 23, 1999

(30) Foreign Application Priority Data

Mar. 13, 1998 (DE) .......................... 198 11 047

(51) Int. Cl.$^7$ ................................. C12P 37/06
(52) U.S. Cl. .................. 435/44; 435/70.3; 435/325; 435/375; 536/23.1; 536/24.5
(58) Field of Search .................. 435/44, 325, 375, 435/70.3, 6; 536/23.1, 24.5

(56) References Cited

FOREIGN PATENT DOCUMENTS

WO          97/04007         2/1997

OTHER PUBLICATIONS

Donato et al., Int J Biochem Cell Biol. Jul. 2001;33(7):637–68.*

Bentley et al., Curr Opin Struct Biol. Dec. 2000; 10(6):637–43.*

Wissler et al., "An Endogenous Bioactive Metallo–Ribonucleo–Polypeptide: A Copper–Containing Monocytic Blood Vessel Morphogen as Novel Type of 'Wound–Hormone'," pp. 385–397 (XP 000614120) (1987).

Wissler et al., "Structure and Function of a Monocytic Blood Vessel Morphogen (Angiotropin) for Angiogenesis in Vivo and In Vitro: A *Copper* –Containing Metallopolyribonucleo–Polypeptide as a Novel and Unique Type of Monokine," (XP 002022899) (Jan. 19, 1987).

Dell Angelica et al., "Primary Structure and Binding Properties of Calgranulin C. a Novel S100–Like Calcium–Binding Protein from Pig Granulocytes," *The Journal of Biological Chemistry*, 269 (46) 28929–28936 (Nov. 18, 1994).

* cited by examiner

Primary Examiner—Sean McGarry
Assistant Examiner—James Douglas Schultz
(74) Attorney, Agent, or Firm—Leydig, Voit & Mayer, Ltd.

(57) ABSTRACT

The present invention relates to metal-containing ribonucleotide polypeptides (RNP) and processes for their production, their use and medicaments containing ribonucleotide polypeptides or their molecular-biological equivalent structures and/or parts and/or derivatives.

5 Claims, 2 Drawing Sheets

Energy-minimised     secondary structure of ARNA I
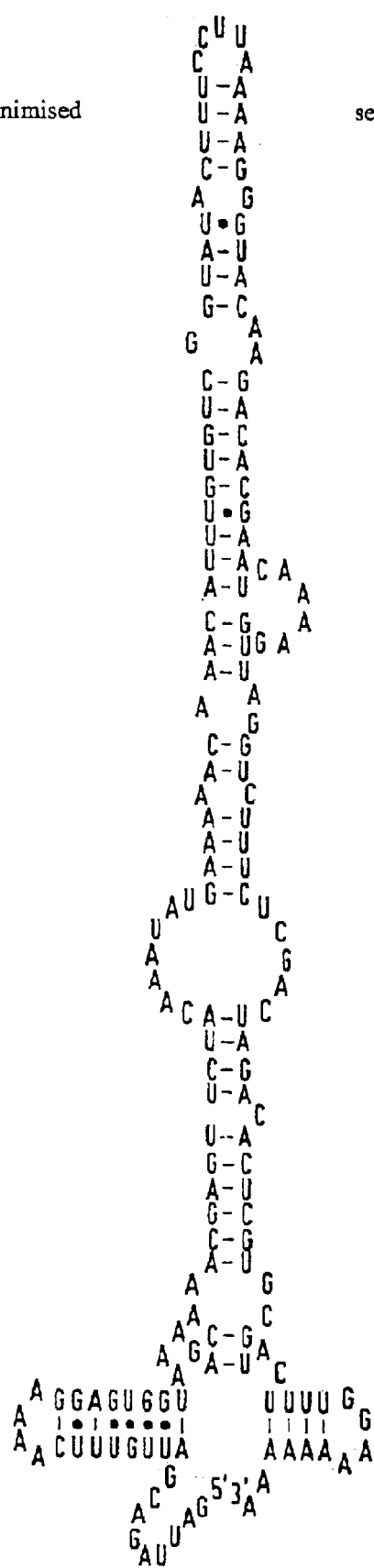

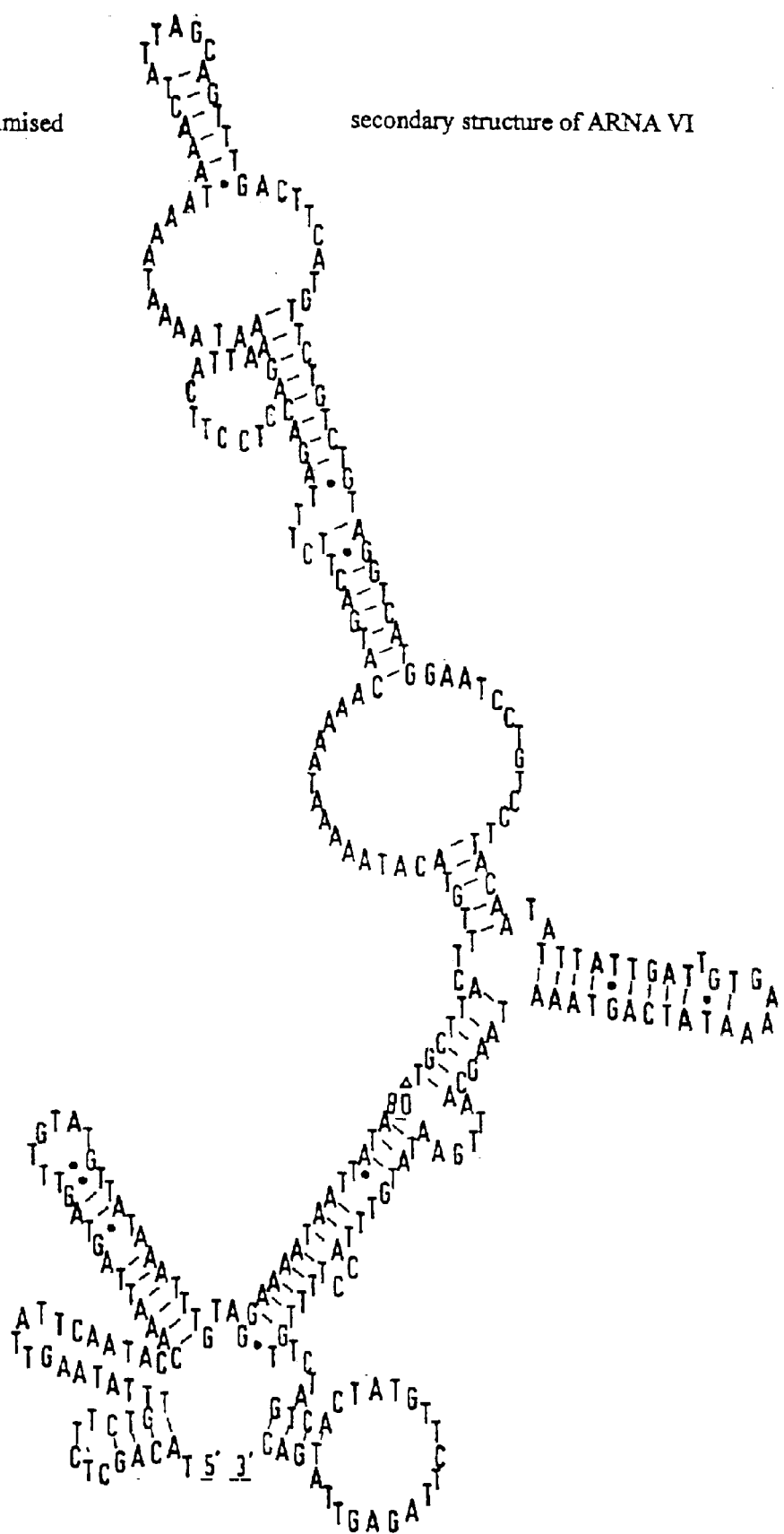

METAL-CONTAINING RIBONUCLEOTIDE POLYPEPTIDES

The present invention relates to metal-containing ribonucleotide polypeptides (RNP) and processes for their preparation, their use and medicaments containing ribonucleotide polypeptides or their molecular-biological equivalent structures and/or parts and/or derivatives.

Tissue homeostasis of the body, its organs and tissue depends on the regulation mechanisms of angiogenesis. This influences both tissue repair and wound healing, formation of new tissue in embryogenesis and the reproductive cycles and growth, retrogression and destruction of tumours, transplants and vascularised and non-vascularised tissues.

Hitherto, no non-mitogenic mediators have yet been found, with which influence of tissue homeostasis is possible, that is induction and regulation of vascular growth.

The object of the present invention is therefore to provide a non-mitogenic mediator of tissue homeostasis, with which primarily tissue repair, wound healing, angiogenesis and neovascularisation may be influenced. A further object of the invention is the provision of a process for producing the non-mitogenic mediators and a medicament containing this non-mitogenic mediator.

These aims are achieved by the objects of the patent claims.

It has been found by the inventors that there are non-mitogenic cellular mediators based on nucleic acid of defined sequence, which may cause specifically the formation of blood vessels in vivo and in vitro and represent biologically specific, naturally acting non-mitogenic mediators of angiogenesis or the directional growth of blood vessel branches.

The new class of cellular morphogens for endothelial cells proven by the inventors exists in the form of a bioactive metal ribonucleotide peptide (RNP). This is called angiotropin.

The structure of angiotropin may be assigned to the ribonucleotide proteins (RNP). It consist of a protein part (ARP=Angiotropin Related Protein) and an RNA part (ARNA=Angiotropin RNA). Cu(II) is essential for formation of the complex of ARP and ARNA. In addition to the copper ion, angiotropin contains a Ca(II) ion. Mg(II) ions are also useful for the diverse biological and biochemical functions of angiotropin.

The protein part (ARP) consists of a protein which may be assigned to the family of S100 proteins (Dell'Angelica et al., Journal of Biological Chemistry, Volume 269, No. 46, page 28929–28936 (1994)) and is preferably 91 amino acids long. The primary structure of this preferred ARP is as follows:

exchanges, insertions or deletions of amino acids, which modify the structure of the protein part, its biological activity being essentially maintained. The exchanges preferably include "conservative" exchanges of amino acid residues, that is exchanges for biologically similar residues, for example the substitution of a hydrophobic residue (for example isoleucine, valine, leucine, methionine) for a different hydrophobic residue, or the substitution of a polar residue for a different polar residue (for example arginine for lysine, glutamic acid for asparaginic acid etc.). Deletions may lead to the production of molecules which have a significantly smaller size, that is those lacking, for example amino acids at the N or C terminus.

The RNA part (ARNA) has the following consensus sequence:

GGAAAAUNNNUN$_{0-1}$AUAUGN$_{0-6}$ CUTNNUUUNNNAAAAN$_{0-1}$UANAAACAUN$_{0-5}$ CUUNAGN$_{0-13}$AGAAAUN$_{0-16}$UUAGCAG wherein "N" is G, A, U, or C, or the complementary sequence thereof.

According to the invention the ARNAs which can be used are further defined as follows:

(A1) ARNA I
Klon-3a (ARNA I)
AAAAAAAAGGUUUUCAUGCGUGCUCACA-GAUCAGCUCUUUCUGGAUUGAAAAGCU AAG-CACAGAACAUGGGAAAAUUCCUUU-CAUAUGGCUGUGUUUACAAACAAAAAGU AUAAACAUCUUGAGCAAACAGAAAUG-GUGAGGAAAACUUUGUUAGCAGAUUAG (SEQ ID NO: 2)
or an RNA which is different therefrom by one or more base pairs or a fragment thereof,
or
(A2) ARNA VI
Kion-P10 (ARNA VI)
UUACAGCUCUUCUGUUUAUAAGUUAUU-CAAUACCAAAUUAGUAGUUUGUAUGUUA UAAAUUUGUAGGAAAAUAA-UUAUAUAUGCUUACUUUGUA-CAUAAAAAUAAAAACAU GACUUCUUUAGA-CACUCCUUCAUUAGAAAUAAAAUAAAAUA AACUAUUAGCAGUUU GACUUCAUGUUCUGU-CUGUAGGUCAUGGAAUCCUGUCCUUA-CAAUAUUUAUUGAU UGUGAAAAUAU-CAGUAAAUAAGCAAUUGAAUAUGUUUACC UUUUCUUCUAGUCAC UAUGUUCUUAGAG-UUAUGACA (SEQ ID NO: 4)
or an RNA which is different therefrom by one or more base pairs or a fragment thereof.

The nucleic acid molecules defined under (a1) (SEQ ID NO:3) and (a2) (SEQ ID NO: 4) so include nucleic acid

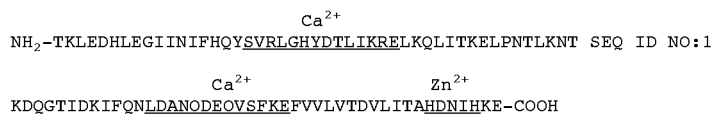

NH$_2$-TKLEDHLEGIINIFHQY$\underline{\text{SVRLGHYDTL}}$IKREL$\underline{\text{KQLITKELPNTLKNT}}$ SEQ ID NO:1

$\quad\quad\quad\quad\quad\quad$ Ca$^{2+}$ $\quad\quad\quad\quad\quad\quad\quad\quad\quad\quad$ Zn$^{2+}$
KDQGTIDKIFQN$\underline{\text{LDANODEOVSFKE}}$FVVLVTDVLITA$\underline{\text{HDNIHKE}}$-COOH It has two EF-hand motives and furthermore a binding site for zinc(II) ions. The dissociation constants $K_D$ of the metal ion complexes are 10.0 $\mu$M for Ca(II) ions or 0.1 $\mu$M for zinc(II) ions and 1.0 $\mu$M for copper(II) ions.

In this context, it should be mentioned that the protein part of the invention may be modified according to conventional processes known in the expert field without the biological activity being lost. These modifications include molecules which are different with respect to the abovementioned sequence due to deletion(s), insertion(s), exchange(s) or other modifications known in the state of the art, without the biological activity being lost. The term "nucleic acid fragment" should include a cutout or segment of the original nucleic acid molecule. Processes for producing the above changes in the nucleic acid sequence are known to the expert and described in standard works on molecular biology, for example in Sambrook et al., Molecular Cloning: A Laboratory Manual, 2nd Edition, Cold Spring Harbor Laboratory Press, Cold Spring Harbor N.Y. (1989).

The ARNAs mentioned also include molecular-biological equivalent structures, that is structures in which individual bases or amino acids are exchanged. They also include therewith hybridising nucleic acids (preferably under stringent conditions, such as 20° C. below the melting point of RNA) or nucleic acids related via the degenerated genetic code.

The RNPs of the invention are characterised by the following properties:

cell-selective morphogenic effect in vitro on isolated, primary and/or cloned blood capillary endothelial cells in culture for non-mitogenic induction of change of the cell phenotype from the confluent state, for non-mitogenic change of the spatio-temporal supracellular organisation of cells to form three-dimensional organoid, capillary-similar structures in culture;

specific chemotropic effect on blood vessels in vivo, induction of directional growth of blood vessels in vivo, induction of neovascularisation of tissues by directed inward growth of blood vessels.

In the RNPs of the invention, the protein part is bound to the RNA part by interactions.

The object of the invention is also a process for producing and recovering the bioactive RNPs, characterised in that the cells, for example the leucocytes or inflammation tissue is homogenised or leucocytes are cultivated and the resulting RNPs are recovered from the homogenates or from the supernatants of the culture solution by standard methods. For example angiotropin may be isolated from the supernatants of serum-free mass cell cultures of concanavaline A-activated porcine blood leucocytes and leucocytes from ischaemic/infarcted heart muscle cells and purified to homogeneity.

The process for producing and recovering the bioactive RNP morphogens of cells or leucocytes and inflammation tissue is characterised in that cells or leucocytes of the reticulo-endothelial system of leucocytes and inflammation tissue, are cultivated and the resulting RNP morphogens are recovered from the homogenates or from the supernatant culture solution.

In principle, it is also possible to work up the cells, for example leucocytes on mediators directly without culture.

Culture of the cells (leucocytes) may be carried out in principle in any medium maintaining the cells (leucocytes).

For the culture of cells, such as leucocytes, in most cases serum, for example calf serum or horse serum, is added to the culture media for a planned duration of culture over 1 hour, since the serum constituents are favourable for the maintenance of the vital functions of the cells. If however the serum-containing culture solution is to be worked up on proteins (mediators), which are produced by the culture, recovery of the product proteins present mostly only in low concentrations creates considerable difficulties due to the number of foreign proteins originating from the serum. In addition, it is thus not possible to establish with certainty whether a certain mediator is of humoral or cellular origin and from which species it comes; that is whether it is a mediator of the species, the cells of which have been cultivated, or the species, from which the serum used (mostly heterologous) comes.

The fully synthetic cell culture medium preferably used according to the invention contains the conventional material groups, such as salts, sugars, amino acid, nucleosides and nucleoside bases, vitamins, vitaminoids, coenzymes and steroids in aqueous solution. It is characterised in that it additionally contains one material or a mixture of several materials, which have proved to be particularly valuable for the vitality and the growth of the leucocytes and their ability for mediator production. These materials include unsaturated fatty acids, flavonoids, ubiquinones, vitamin C and mevalolactone.

The cell culture medium is used for longer-lasting cell or leucocyte culture, preferably without adding serum. Instead, it has at least one defined protein, which is highly pure, molecularly uniform serum albumin in a particularly preferred embodiment.

In further preferred embodiments, the fully synthetic serum-free cell culture medium used according to the invention may contain still further compounds which are favourable for the culture of leucocytes from the material classes of polyhydroxy compounds and sugars, amino acids, nucleosides, anionic compounds and/or vitamins, the use of which is not conventional in the known culture media. The constituents of the medium used according to the invention are adjusted to one another with regard to their quantitative proportions so that the concentration of the components in the medium is largely matched to the natural concentration ranges of the plasma; see Ciba-Geigy AG (Publisher) (1969) in Documenta Geigy, Wissenschaftliche Tabellen [Scientific Tables], 7th Edition Geigy S. A., Basle.

The cell culture medium is preferably free of surfactants, heavy metal salts and dyestuffs which damages cells and may disturb the recovery of the required cell products from the culture solution.

The cell culture medium having the composition indicated in Table 1 below is particularly preferred for the culture of the leucocytes in the process of the invention.

Water having ATM-1 quality is used for producing the medium; see ASTM D-1193-70 Standard Specification for Reagent Water 1970; Annual Book of ASTM Standards, Easton Md., ASTM 1970. Furthermore, it is freed of possible endotoxin contaminations due to ultrafiltration on surfactant-free membranes having the exclusion limit of 10,00 Dalton. The final medium is filter-sterilised on surfactant-free membranes having $\leq 0.2$ μm pore size.

TABLE 1

| No. | Component | mole/liter |
|---|---|---|
| 1 | KCl | 5.0 m |
| 2 | $KH_2PO_4$ | 0.2 m |
| 3 | NaCl | 120.0 m |
| 4 | $Na_2HPO_4$ | 0.8 m |
| 5 | $Na_2SO_4$ | 0.8 m |
| 6 | L-Ascorbic acid | 0.2 m |
| 7 | Choline chloride | 50.0 μ |
| 8 | 2-Deoxy-D-ribose | 5.0 μ |
| 9 | D-Galactose | 0.5 m |
| 10 | D-Glucose | 5.0 m |
| 11 | D-Glucurono-γ-lactone | 0.1 m |
| 12 | Glycerol | 50.0 μ |
| 13 | myo-Inositol | 0.5 m |
| 14 | Na acetate | 0.2 m |
| 15 | Na citrate | 50.0 μ |
| 16 | Na pyruvate | 0.1 m |
| 17 | D-Ribose | 20.0 μ |
| 18 | Succinic acid | 0.1 m |
| 19 | Xylitol | 10.0 μ |
| 20 | D-Xylose | 20.0 μ |
| 21 | $CaCl_2$ | 2.0 m |
| 22 | $MgCl_2$ | 1.0 m |
| 23 | $NaHCO_3$ | 10.0 m |
| 24 | Human serum albumin | 7.7 μ |
| 25 | Penicillin | 1.0 μ |

TABLE 1-continued

| No. | Component | mole/liter |
|---|---|---|
| 26 | Streptomycin | 2.0 μ |
| 27 | L-Glutamine | 1.0 m |
| 28 | L-Alanine | 0.2 m |
| 29 | L-Asparagine | 0.1 m |
| 30 | L-Asparaginic acid | 0.1 m |
| 31 | L-Glutamic acid | 0.1 m |
| 32 | Glycine | 0.2 m |
| 33 | L-Proline | 0.1 m |
| 34 | 2L-Serine | 0.1 m |
| 35 | L-Arginine | 0.1 m |
| 36 | 4-Aminobenzoic acid | 2.0 μ |
| 37 | L-Cysteine | 0.2 m |
| 38 | L-Histidine | 0.1 m |
| 39 | L-Hydroxyproline | 10.0 μ |
| 40 | L-Isoleucine | 0.2 m |
| 41 | L-Leucine | 0.2 m |
| 42 | L-Lysine HCl | 0.2 m |
| 43 | L-Methionine | 0.1 m |
| 44 | L-Ornithine | 50.0 μ |
| 45 | L-Phenylalanine | 0.1 m |
| 46 | Sarcosine | 50.0 μ |
| 47 | Taurine | 0.1 m |
| 48 | L-Threonine | 0.2 m |
| 49 | L-Tryptophane | 50.0 μ |
| 50 | L-Tyrosine | 0.1 m |
| 51 | L-Valine | 0.2 m |
| 52 | Glutathione reduced | 3.0 μ |
| 53 | Carnosine | 5.0 μ |
| 54 | Mevalolactone | 5.0 μ |
| 55 | Adenine | 50.0 μ |
| 56 | Adenosine | 50.0 μ |
| 57 | Citidine | 50.0 μ |
| 58 | Guanine | 5.0 μ |
| 59 | Guanosine | 20.5 μ |
| 60 | Hypoxanthine | 5.0 μ |
| 61 | 5-Methylcytosine | 5.0 μ |
| 62 | Thymidine | 20.0 μ |
| 63 | Thymine | 5.0 μ |
| 64 | Uracil | 5.0 μ |
| 65 | Uridine | 20.0 μ |
| 66 | Xanthine | 5.0 μ |
| 67 | Biotin | 1.0 μ |
| 68 | C-Ca pantothenate | 5.0 |
| 69 | Ergocalciferol | 0.5 μ |
| 70 | D, L-Carnitine | 50.0 μ |
| 71 | Folic acid | 5.0 μ |
| 72 | D, L-α-lipoic acid | 2.0 μ |
| 73 | Menadione | 0.2 μ |
| 74 | Nicotinamide | 20.0 μ |
| 75 | Pyridoxal HCl | 5.0 μ |
| 76 | Pyridoxine HCl | 2.0 μ |
| 77 | Riboflavin | 1.0 μ |
| 78 | Rutin | 5.0 μ |
| 79 | Thiamine HCl | 5.0 μ |
| 80 | D, L-α-tocopheryl acetate | 1.0 μ |
| 81 | Vitamin A acetate | 1.0 μ |
| 82 | Vitamin K | 0.2 μ |
| 83 | Vitamin $B^1$ | 0.5 μ |
| 84 | Vitamin $U^{12}$ | 1.0 μ |
| 85 | Cholesterol | 1.0 μ |
| 86 | Coenzyme $Q_{10}$ | 0.1 μ |
| 87 | Linolic acid | 1.0 μ |
| 88 | Linolenic acid | 5.0 μ |
| 89 | Oleic acid | 5.0 μ |
| 90 | Ethanol | 1.0 m |
| 91 | pH 7.10 | — |
| 92 | Concanavaline A | 50.0 n |

Depending on the type of products required, either mixed cell or leucocyte populations or individual cell or leucocyte types are cultivated. The production and culture of the cells or leucocytes must be effected under sterile conditions. Culture is carried out for a sufficiently long time to obtain a satisfactory mediator yield. A period of about 10 to 50 hours has proved to be suitable for this. With shorter times, the mediator yield is too low, so that the process is uneconomical. On the other hand, for a culture period over about 50 hours, the medium is spent and the cells start to die off, so that an increase in yield can no longer be expected.

Culture of the cells or leucocytes is carried out at a temperature of about 30 to 42° C., preferably about 37° C. At lower temperatures the culture process is unsatisfactory, whereas at temperatures above 42° C. the leucocytes are damaged.

Culture is carried out at a concentration of about $10^6$ to $5 \times 10^8$ cells/ml, preferably up to $10^7$ to $10^8$ cells/ml. At lower cell concentrations, the yield per unit volume of culture solution is too low. The process becomes uneconomical due to large culture volumes. At cell concentration above $5 \times 10^8$ cells/ml, there is very rapid reduction of nutrients in the medium.

Culture may be carried out in the atmosphere. An increased carbon dioxide partial pressure is preferably maintained above the culture and may reach to about 10 volume %, in particular to about 2 volume %. The oxygen supply to the culture is of considerable importance. It may be ensured, for example by introducing air. In order to avoid contamination of the culture, the air supplied is preferably sterilised and decontaminated by heat, that is freed of endotoxins and other organic constituents. The solution may be stirred or shaken during culture. Con A is preferably used as cell stimulant.

To complete the culture, the cells or leucocytes are centrifuged off from the culture solution, which is then worked up on the resulting angiotropins. In order to avoid damage to the cells and hence contamination of the culture solution due to cell constituents, the culture is centrifuged at relatively low acceleration, that is about 300 to 400×g. After separating off the greater portion of the cells from the supernatant, the latter is advantageously centrifuged again at higher acceleration to remove residual suspended particles. The leucocytes separated off may either be cultivated again, cryopreserved or passed to a different use.

Apart from culture of leucocytes, the bioactive RNP morphogens of the invention may also be recovered from inflammation tissue. They are produced there due to the accumulation of leucocytes as a result of the inflammation process triggered by tissue damage. The inflammation tissue may be recovered in conventional manner and used for the preparation of RNP. The inflammation tissue is thus homogenised in buffer solution and the soluble constituents (exudate) are separated from the insoluble structural constituents of the tissue.

Inflamed, infarcted heart muscle tissue, which is formed by ligation of the left front descending branch of the left coronary artery by means of a transfemoral catheter technology for 24 hours, is preferably used. The inflamed heart muscle part containing leucocytes is separated off at 0 to 4° C. from non-infarcted, healthy tissue.

The working up of a very large culture solution volume is required for the isolation and recovery of the bioactive RNP of the invention. It is therefore necessary for practical reasons at the start of the purification process to carry out as effective as possible reduction of the volume to be treated. The culture solution contains the mixture of the constituents of the medium in addition to the small quantities of substances produced, including mainly proteins. Separation of the proteins produced from the constituents of the medium and at the same time from the large volume of aqueous solution, is therefore advantageously carried out in the first step of purification. This may be effected by selective salting-out of the proteins from the culture solution, which is achieved, for example by adding a sulphate or phosphate.

Precipitation of the proteins using the example of salting-out by adding ammonium sulphate to the culture solution is described below.

A large portion of the proteins produced, together with optionally present serum albumin, is precipitated by saturation of the culture solution with ammonium sulphate. After separating off the substance precipitate, for example by centrifuging, the latter may be separated into its individual components in the manner described below and the bioactive RNP present recovered. The supernatant obtained also contains the part of the substances which are soluble in saturated ammonium sulphate solution, also including part of the bioactive RNP, in addition to the soluble constituents of the medium. The supernatant is concentrated and the substances present are recovered therefrom in the manner below. If the protein-containing culture solution is treated to saturation with ammonium sulphate, the larger part of the concomitant proteins is precipitated. A protein mixture, which consists of a number of different proteins and the separation of which into the individual components is consequently laborious, is obtained in this manner. In a preferred embodiment of the process of the invention, the protein mixture present in the culture solution is therefore already separated into several fractions in the precipitation stage. This separation into several protein fractions is possible, since the individual proteins are precipitated at different ammonium sulphate concentrations. The culture solution in the process of the invention is therefore preferably treated in stages with ammonium sulphate up to certain degrees of saturation, wherein in each fraction the part of the proteins precipitates, the solubility product of which lies below the particular degree of saturation. In the process of the invention, coarse separation into groups of proteins may be achieved even during precipitation by suitable selection of saturation limits of the individual fractions.

By way of example, the culture solution is initially treated with ammonium sulphate up to a saturation of 35%. The protein precipitate obtained is separated off. The degree of saturation of the supernatant solution is then increased to 45%. A protein precipitate is formed again, which is separated off. The supernatant solution is then set to a degree of saturation of 90%. The protein precipitate thus obtained is likewise separated off. The supernatant solution of this precipitate is concentrated, for example by water-removing dialysis or ultrafiltration.

Salt precipitation of the proteins is carried out, as is the subsequent purification, preferably at a temperature of about 0 to 10° C., in particular about 0 to 4° C. The solutions used for purification have a pH value between 5 and 9, in particular between 6 and 8. In order to achieve pH constancy for the solution, a strong buffer, for example 0.1 mole/liter phosphate buffer, is preferably added before salt precipitation. To maintain the redox potential of the proteins, cysteine is preferably added to the solutions in a quantity of 0.001 mole/liter. Sterile conditions for protein purification are not necessary.

The proteins obtained during salt precipitation may be passed directly to purification and separation described below after dissolving in a medium which does not damage proteins. The supernatant of the last precipitation step is concentrated, for example by water-removing dialysis or ultrafiltration. All compounds having a molecular weight of more than about 300 to 500 Dalton, that is also the proteins and peptides of this fraction, are thus obtained quantitatively as retentate.

The protein fractions obtained in the stage described above contain the bioactive RNP of the invention mixed with numerous foreign proteins (other secreted proteins optionally serum albumin and optionally CON). The foreign proteins exist in by far the predominant quantity in the mixtures. The bioactive RNP has to be enriched by a series of purification steps and freed of the foreign proteins until they no longer disturb their molecular biological specificity. The bioactive RNP themselves are likewise a material class, which is divided into its individual, specifically acting individual parts.

Purification processes for albuminous substances (proteins) and other natural materials generally consist of a sequence of combined separation processes, which utilise differences in molecular size, charge, shape, structural stability and molecular surface condition between the required active ingredient and the concomitant foreign materials for separation. Accordingly, numerous combinations of the widest variety of separation processes may be worked out for purification of a protein. For managing properties, technical feasibility, ability for automation and economic viability of a purification process and for the quality of the required natural product, therefore not only is the type of separation steps used important, but in particular their optimised arrangement and their useful combination in a purification sequence within the framework of the structural stability and the other structural parameters of the required active ingredient. This also means that even the use of the same or similar separation principles (for example molecular sieve filtration, dialysis, ion-exchange adsorption, etc.), but in different combination, may be crucial for the manageability and economic viability of the purification process. In certain cases, the use or omission of a single technology (for example hydroxylapatite chromatography, zone precipitation chromatography, etc.) is of decisive significance at a certain point of the purification sequence, or within a limited part sequence, for the quality of the required active ingredient and for the manageability and the economic viability of its purification process. These general contexts and basic principles of natural material purification are clearly shown, for example by the generally known fact that in an economically sensible and technically manageable natural material purification process, a column chromatography purification step or a lyophilisation step is not useful, before the total output volume or the output concentration of the concomitant foreign constituents of the active ingredient raw extract has not been reduced to at least 1/500 to 1/1,000 by other process steps.

A plurality of purification steps known individually per se in biochemistry is offered for purification of the individual protein fractions. Examples of such purification steps are: preparative and analytical molecular sieve filtration, anion and cation exchange chromatography or one-pot adsorption processes, chromatography on hydroxylapalite, zone precipitation chromatography and circulation or cascade molecular sieve filtration.

A considerable quantity of concomitant protein may be separated off from the bioactive RNP even by single implementation of one of the said purification processes. However, the substances present in the fractions often adhere very strongly to one another in spite of their different molecular weight. They are often separated incompletely according to their molecular weight, for example in molecular sieve filtration by the existence of non-ideal equilibria for protein polyelectrolytes. It is therefore advisable to carry out at least two of the said separating processes one after another. The protein fractions containing the bioactive RNP activity are preferably subjected to at least three of the said purification steps one after another.

All combinations of the separating steps mentioned are the object of the process of the invention. It is part of the level of knowledge of the expert that certain results of separating steps are less useful than other combinations. For example the expert knows that when carrying out a preparative molecular sieve filtration after an analytical molecular sieve filtration, in addition to the unwieldy procedure, a poorer overall result with respect to the separating effect is also obtained than for the reverse sequence.

Molecular sieve filtration effects separation of the proteins according to their molecular weight. Since a predominant part of the concomitant foreign proteins has a different molecular weight to the bioactive RNP, their separation may be achieved in this manner. A hydrophilic molecular sieve which swells in water is used for separation of the substances according to their molecular weight. Examples of suitable molecular sieves are dextrans crosslinked using epichlorohydrin (sephadex), agaroses crosslinked using acrylamide (Ultrogels) and spatially crosslinked acrylamides (biogels), the exclusion limits of which are greater than the separation limits used for separation.

Molecular sieve filtration is preferably carried out as one of the first separating stages, if several separating stages are used. Depending on the length-diameter ratio of the columns used and the particle diameter of the gel matrix, which influence the theoretical number of plates of the column, molecular sieve filtration is designated as "preparative" or "analytical". It is designated as "preparative" if chromatography is carried out on columns having a dimensional ratio length:diameter up to 10:1 and a charge of up to ⅓ of the column content or with full utilisation of the total, matrix-typical separation volume. "Analytical" means an length-diameter ratio above 10:1, preferably about 50:1, and a charge up to a maximum 3% of the column content, even for HPLC versions.

In preparative molecular sieve chromatography, gel matrices having as large as possible particle size are used to achieve rapid throughflow rates of the often somewhat viscous protein solutions at as low pressures as possible. In analytical molecular sieve filtration, the particle size of the gel matrix is selected to be as small as possible to achieve a maximum theoretical number of plates for the column at technically and, in terms of safety, acceptable pressure and a flow rate for the mobile phase of 2 to 4 cm/hour. These parameters depend on the gel matrix structure and are different from gel to gel.

If several preparative molecular sieve filtrations are carried out one after another, the separation limit may be selected to be graded. Analytical molecular sieve filtration with correspondingly graded separation limits may be carried out following that. The exclusion limit of the gel used must in any case be greater than about 10,000 Dalton to facilitate volume distribution of the angiotropins between the stationary gel matrix phase and the mobile aqueous buffer phase.

The "exclusion limit" designates the hydrodynamic parameter of a dissolved particle, which corresponds to the pore size of the gel matrix. Particles having greater hydrodynamic parameter can no longer penetrate into the gel matrix (volume distribution coefficient $K_D$=0). The "separation limit" designates a hydrodynamic parameter advantageously fixed to separate dissolved particles, and which lies between a volume distribution coefficient $K_D$=0 and $K_D$=1.

For molecular sieve filtration, the substances are dissolved in a liquid, which does not damage the substances, applied to the molecular sieve. A specific example of a suitable solvent is 0.003 mole/liter sodium potassium phosphate solution containing 0.3 mole/liter NaCl and 0.001 mole/liter cysteine and having a pH value of 7.4. After filtration, the fractions containing RNT are concentrated in the manner described below, and optionally subjected to a further purification step.

Suitable anion exchangers for purification of the substances are, for example dextran crosslinked using epichlorohydrin (sephadex) or cellulose matrices, to which functional groups having anion exchange capacity are coupled. They may be used again after use due to regeneration. An equilibrated, weak anion exchanger pre-swollen in a buffer solution in the Cl form, such as DEAE-sephadex-A 50, is preferably used and the treatment is carried out at a pH value of 8 to 10. A specific example of such a buffer solution is 0.01 mole/liter tris HCl, which contains 0.04 mole/liter NaCl and 0.001 mole/liter cysteine and has a pH value of 8.0.

When using the anion exchanger, the substance fraction of such a quantity of anion exchanger is added, which is adequate for complete adsorption of the angiotropins and the positively adsorbed concomitant proteins. Two parts by volume of swollen anion exchangers conventionally suffice for this per volume of concentrated protein fraction. The reaction may be designed either as a chromatography process or as an easier to manage one-pot adsorption process. In the one-pot process, the supernatant liquid with the negatively adsorbed proteins is separated from the anion exchanger charged with the positively adsorbed RNP and other substances, for example by filtering (in the chromatography column), decanting or centrifuging (in the one-pot process). The charged anion exchanger is freed of adhering, negatively adsorbed compounds by washing with water or a salt solution, which has a maximum ion strength equivalent to 0.04 mole/liter NaCl, preferably at the most about 15° C. A specific example of a salt solution suitable for washing out is the tris HCl buffer solution mentioned of pH value 8.0.

The anion exchangers charged with RNP and other substances and freed of negatively adsorbed compounds is now eluted using an aqueous salt solution which does not damage proteins, and which has a corresponding ion strength greater than 0.04 mole/liter NaCl and a pH value between 4.0 and 10.0. A salt solution of high ion strength having a pH value of 5.0 to 7.0 is preferably used. A specific example of such a salt solution is a 2.0 mole/liter NaCl solution, which is buffered with 0.01 mole/liter piperazine HCl around pH value 6.5 and which contains 0.001 mole/liter cysteine.

If the anion exchange reaction is designed as a chromatography process, elution of the RNP and other substances may also be effected by a linear NaCl concentration gradient.

Suitable cation exchangers for purification of the protein fraction are, for example dextran crosslinked with epichlorohydrin (sephadex) or cellulose matrices, to which functional groups having cation exchange capacity are coupled. They may be used again after use due to regeneration. A weakly acidic cation exchanger in the Na$^+$ form, such as CM-sephadex C-50, is preferably used, and the treatment is carried out at a pH value of 4 to 6. The substance fractions may be diluted to facilitate adjustment of the charge equilibria before treatment with the cation exchanger using a salt solution which does not damage proteins, and which has a maximum ion strength equivalent to 0.04 mole NaCl/liter. It may serve at the same time for adjusting the pH value. A specific example of such a salt solution is a 0.001 mole/liter potassium phosphate acetate buffer solution containing 0.04 mole/liter NaCl and having a pH value of 4 to 6. This cation exchange reaction may be permitted both as a chromatography process and as a technically easily manageable one-pot process.

The cation exchanger is added to the substance fraction in a quantity which is adequate to adsorb the protein fraction. About 2 parts by volume of swollen ion exchanger per part by volume of protein fraction conventionally suffice therefor. The supernatant liquid is then separated off from the cation exchanger charged with the substances, for example by decanting or centrifuging. The charged cation exchanger is freed of adhering, non-adsorbed compound by washing with water or a salt solution, which has a maximum ion strength equivalent in 0.04 mole/liter NaCl, preferably at a pH value of about 4 to 6 and a temperature of preferably at most about 15° C. A specific example of a salt solution suitable for washing out is the potassium phosphate acetate buffer solution mentioned of pH value 5.0.

The cation exchangers charged with the substances and freed of negatively adsorbed compounds is now eluted using an aqueous salt solution which does not damage proteins and nucleic acids. A salt solution of high ion strength having a pH value of 4 to 10 is preferably used for this. Specific examples of such salt solutions are an aqueous 0.5 mole/liter potassium phosphate solution of pH value 6.5 to 7.5 or a 2 to 5 mole/liter sodium chloride solution of the same pH value.

For chromatography on hydroxylapatite, salts possibly present from preceding steps, for example ammonium sulphate and above all phosphates, are removed before application to the hydroxylapatite, preferably by dialysis or ultrafiltration on a membrane having an exclusion limit of 500 Dalton. Apart from the increase in viscosity due to foreign additives however, only the phosphate concentration of the protein solution is critical for succeeding in chromatography on hydroxylapatite. Elution of the substances takes place due to a potassium phosphate concentration gradient, which is preferably linear. The fractions containing RNP are collected and concentrated in the manner mentioned below.

The use of hydroxylapatite is of considerable importance for the structure-protecting pure recovery of RNP. However, it is associated with considerable difficulties, for technical and economic reasons, to chromatograph larger substance volumes on hydroxylapatite columns. On the one hand, hydroxylapatite tends namely to clog very severely for larger substance volumes and thus becomes unusable. On the other hand, hydroxylapatite is expensive, which stands in the way of its use on a larger scale. For these reasons, it is preferred in the process of the invention to separate off a large part of the concomitant foreign proteins by suitable process steps from the substance fractions, in which the bioactive RNP are present as traces, even before chromatography on hydroxylapatite, and thus to reduce decisively the protein volume, which has to be applied to the hydroxylapatite column.

In zone precipitation chromatography (see J. Porath, Nature, Volume 196 (1962), page 47–48), protein impurities of bioactive RNP are separated off by salting out fractionation of the proteins by means of a salt concentration gradient.

The basic principle of protein separation by means of zone precipitation chromatography is the different, structure-related reversible solubility properties of proteins. They belong to the most sensitive molecular separation parameters and have often been used as a criterion for the detection of molecular uniformity of a protein. Hence, temperatures and pH value, dimension of the column, type of salt, shape of the gradient and charge of the column may be varied within a relatively wide range.

The temperature for zone precipitation chromatography may be about 0 to 40° C. A temperature range from about 0 to 10° C., in particular about 4 to 6° C., is preferred. The pH value may lie between about 4 and 10, a pH value is preferably in the range from 6 to 8, in particular about 7. The ratio of length:diameter of the column used should be greater than about 10:1, a ratio of 30 to 100:1, in particular about 50:1, is preferred. Suitable salts are all salts with effect which do not damage proteins and nucleic acids. Examples of such salts are sodium potassium phosphate, ammonium sulphate and sodium sulphate. Ammonium sulphate is preferably used.

The salt concentration gradient may have any shape, as long as the salting-out points of the proteins are separated according to migration path. Linear concentration gradients, in particular a rising linear concentration gradient of 25 to 100% ammonium sulphate saturation, are preferred. Charging of the column is at the most about 5%, preferably about 1%.

Circulation or cascade molecular sieve filtration may be carried out under the conditions which are described above for analytical molecular sieve filtration. The same molecular sieves and the same column conditions may be used. Sephadex G 50 is preferred for a length-diameter ratio for the column of at least about 50:1 and a charge at the most of about 3% of the column content. The solvents used in analytical molecular sieve filtration are preferably used as solvent and for elution.

In circulation molecular sieve filtration, the eluate is recirculated into the same column at the fixed separation limits. The migration path of the proteins is extended differentially in this manner. In a different embodiment, cascade molecular sieve filtration, the eluate is passed to a new column with the same or similarly defined parameters at the fixed separation limits.

The substance solutions obtained containing bioactive RNP may be purified of undesirable salts and concentrated to give subsequent fractionations of the proteins between the purification steps illustrated above. This concentration (separation of the large part of the aqueous salt solution from the proteins) may be effected in a different manner. For example, the bioactive RNP and the concomitant substances may be concentrated by ultrafiltration or water-removing dialysis on a membrane with the exclusion limit 500 Dalton or by lyophilisation. Molecular sieve filtration may thus also be used modified in conventional manner by selecting the appropriate mobile phase. For molecular sieve filtration, about 0.4 mole/liter ammonium sulphate is preferably added to the substance solution. In contrast to higher concentrations, the ammonium sulphate at this concentration has a strong salting-down effect with respect to proteins. As a result of these measures, the proteins are accordingly kept in solution during molecular sieve filtration. Furthermore, ammonium sulphate prevents bacterial growth and inhibits certain enzymes. Hence it contributes to stabilisation of the bioactive RNP, particularly if chromatography is carried out at higher temperatures (above about 20°) and under non-sterile conditions.

The temperature and pH conditions are not particularly critical when carrying out the purification steps. If maintaining the native conformation of the substances is intended, maintenance of a temperature in a range from about 0 to 8° C., preferably about 0 to 4° C., is advisable. Furthermore, the separation and purification stages have to be carried out under essentially physiological pH and salt conditions. A considerable advantage of the process of the invention consists in that the maintenance of these conditions is easily possible for the first time. The substance solution is preferably also treated with about 0.001 mole/liter cysteine to prevent oxidation.

The bioactive RNP obtained may be stored in a buffered physiological salt solution, for example in 0.0015 mole/liter sodium potassium phosphate solution containing 0.15 mole/ (0.9%) NaCl and 0.001 mole/liter cysteine and having a pH value of 7.4, after conventional filter sterilisation (0.2 μm pore width), naturally and biologically active even at room temperature (for at least 200 hours) or frozen at −25° C. (for at least 5 years). This stability of the bioactive RNP may be regarded, inter alia, as one of the criteria for its highly pure state.

The RNP of the invention may also be produced using chemically or biologically synthesised partial sequences or parts and homologous sequences thereof. It is preferable if the chemically or biologically synthesised oligonucleotides or anti-sense nucleotide sequences in vivo or in vitro, which code partial sequences given according to claim 1, having at least 6 bases are used in the PCR reaction, or anti-sense bioprocess technology is used.

The examples illustrate the invention. The examples describe the recovery of RNP morphogens starting from leucocytes from porcine blood. However, the invention is not restricted to this embodiment. Cells from the reticulo-endothelial system or inflammation tissue, wound tissue or fluid (exudate) of other mammals may also be used.

A further object of the present invention is an antibody directed against an above protein or fusion protein or a partial sequence thereof The antibodies may be monoclonal, polyclonal or synthetic antibodies or fragments thereof, for example Fab, Fv or soFv fragments. They are preferably monoclonal antibodies. For production it is favourable to immunise animals, in particular rabbits or chickens for polyclonal antibodies and mice for monoclonal antibodies, with an above (fusion) protein or fragments thereof. Further "boosters" may be given to the animals using the same (fusion) protein or fragments thereof. The polyclonal antibody may then be obtained from the serum or egg yolk of the animals. The antibodies of the invention may be produced according to standard processes, wherein the protein coded by the nucleic acid molecules of the invention or a synthetic fragment thereof serve as immunogen.

Monoclonal antibodies may be produced, for example by the process described by Kohler and Milstein (Nature 256 (1975), 495) and Galfré, Meth. Enzymol. 73 (1981), 3, wherein mice myeloma cells are fused with spleen cells originating from immunised mammals. These antibodies may be used, for example for immunoprecipitation of the RNPs discussed above or for isolating related structures. The antibodies may be bound, for example in immunoassays in liquid phase or to a solid carrier. The antibodies may thus be marked in different ways. Suitable markers and marking processes are known in the expert field. Examples of immunoassays are ELISA and RIA.

The present invention also relates to the use of the RNPs described above and/or antibodies as medicaments. These medicaments optionally additionally contain a pharmaceutically acceptable excipient. Suitable excipients and the formulation of such medicaments are known to the expert. Suitable excipients include, for example phosphate-buffered saline solutions, water, emulsions, for example oil/water emulsions, wetting agents, sterile solutions etc. The administration of the medicaments may be effected orally or parenterally. The processes for parenteral administration include the topical, intra-arterial (for example directly to the tumour), intramuscular, subcutaneous, intramedullary, intrathecal, intraventricular, intravenous, intraperitoneal or intranasal administration. Suitable dose is determined by the treating physician and depends on varios factors, for example on the age, the sex, the weight of the patient, the type of administration etc. In a preferred embodiment, the RNPs of the invention may be given individually or as a mixture locally for mammals, for example humans, in a quantity of >1 fmole. The threshold dose of efficacy in vivo is >50 fmoles, preferably 2.5 fmoles. These medicaments are suitable for specifically influencing angiomorphogenesis and the vascular state of a tissue of a body of a mammal. These medicaments may also contain at least one anti-RNP immunoglobulin and/or molecular-biological equivalent structures to fulfil the same tasks. The resulting medicament is preferably used for functional influencing of angiogenesis.

The unvention is further descriged using the figures, which show:

FIG. 1 Energy-minimised secondary structure of ARNA I (SEQ ID NO: 2)

FIG. 2 Energy-minimised secondary structure of ARNA VI (SEQ ID NO: 3)

What is claimed is:

1. An isolated or purified metal-containing ribonucleotide protein (RNP) containing a protein from the family of S100 proteins, an RNA and a copper ion, wherein the RNP is in the form of a ternary complex, wherein the RNA has a nucleotide sequence having a consensus nucleotide sequence of SEQ ID NO: 2, and wherein the protein from the family of S100 proteins (i) has the amino acid sequence of SEQ ID NO: 1, (ii) has two EF hand motifs and a zinc(II) ion binding site and (iii) specifically binds to the RNA.

2. A process for producing an isolated or purified metal-containing RNP according to claim 1, characterized in that leucocytes or inflammation tissue is homogenized or leucocytes are cultivated and the resulting RNP is recovered from the homogenates or from the supernatant of the culture solution by standard methods.

3. The isolated or purified metal-containing RNP of claim 1, wherein the nucleotide sequence having a consensus nucleotide sequence of SEQ ID NO: 2 is SEQ ID NO: 3.

4. The isolated or purified metal-containing RNP of claim 3, wherein the protein has the amino acid sequence of SEQ ID NO: 1.

5. A medicament comprising the metal-containing RNP of claim 1.

* * * * *

SEQUENCE LISTING

```
<160> NUMBER OF SEQ ID NOS: 4

<210> SEQ ID NO 1
<211> LENGTH: 91
<212> TYPE: PRT
<213> ORGANISM: Unknown
<220> FEATURE:
<221> NAME/KEY: misc_feature
<222> LOCATION: ()..()
<223> OTHER INFORMATION: Angiotropin-related protein

<400> SEQUENCE: 1

Thr Lys Leu Glu Asp His Leu Glu Gly Ile Ile Asn Ile Phe His Gln
 1               5                  10                  15

Tyr Ser Val Arg Leu Gly His Tyr Asp Thr Leu Ile Lys Arg Glu Leu
            20                  25                  30

Lys Gln Leu Ile Thr Lys Glu Leu Pro Asn Thr Leu Lys Asn Thr Lys
        35                  40                  45
```

```
Asp Gln Gly Thr Ile Asp Lys Ile Phe Gln Asn Leu Asp Ala Asn Gln
         50                  55                  60

Asp Glu Gln Val Ser Phe Lys Glu Phe Val Val Leu Val Thr Asp Val
 65                  70                  75                  80

Leu Ile Thr Ala His Asp Asn Ile His Lys Glu
                 85                  90

<210> SEQ ID NO 2
<211> LENGTH: 107
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (8)..(8)
<223> OTHER INFORMATION: N is nucleotide A, C, U, or G
<220> FEATURE:
<221> NAME/KEY: misc_feature
<222> LOCATION: (9)..(9)
<223> OTHER INFORMATION: N is nucleotide A, C, U, or G
<220> FEATURE:
<221> NAME/KEY: misc_feature
<222> LOCATION: (10)..(10)
<223> OTHER INFORMATION: N is nucleotide A, C, U, or G
<220> FEATURE:
<221> NAME/KEY: misc_feature
<222> LOCATION: (11)..(11)
<223> OTHER INFORMATION: N is nucleotide A, C, U, or G
<220> FEATURE:
<221> NAME/KEY: misc_feature
<222> LOCATION: (12)..(12)
<223> OTHER INFORMATION: N is nucleotide A, C, U, or G
<220> FEATURE:
<221> NAME/KEY: misc_feature
<222> LOCATION: (14)..(14)
<223> OTHER INFORMATION: N is nucleotide A, C, U, or G and may or may
      not be present
<220> FEATURE:
<221> NAME/KEY: misc_feature
<222> LOCATION: (20)..(20)
<223> OTHER INFORMATION: N is nucleotide A, C, U, or G and may or may
      not be present
<220> FEATURE:
<221> NAME/KEY: misc_feature
<222> LOCATION: (21)..(21)
<223> OTHER INFORMATION: N is nucleotide A, C, U, or G and may or may
      not be present
<220> FEATURE:
<221> NAME/KEY: misc_feature
<222> LOCATION: (22)..(22)
<223> OTHER INFORMATION: N is nucleotide A, C, U, or G and may or may
      not be present
<220> FEATURE:
<221> NAME/KEY: misc_feature
<222> LOCATION: (23)..(23)
<223> OTHER INFORMATION: N is nucleotide A, C, U, or G and may or may
      not be present
<220> FEATURE:
<221> NAME/KEY: misc_feature
<222> LOCATION: (24)..(24)
<223> OTHER INFORMATION: N is nucleotide A, C, U, or G and may or may
      not be present
<220> FEATURE:
<221> NAME/KEY: misc_feature
<222> LOCATION: (25)..(25)
<223> OTHER INFORMATION: N is nucleotide A, C, U, or G and may or may
      not be present
<220> FEATURE:
<221> NAME/KEY: misc_feature
<222> LOCATION: (28)..(28)
<223> OTHER INFORMATION: N is nucleotide A, C, U, or G
<220> FEATURE:
<221> NAME/KEY: misc_feature
<222> LOCATION: (29)..(29)
```

-continued

```
<223> OTHER INFORMATION: N is nucleotide A, C, U, or G
<220> FEATURE:
<221> NAME/KEY: misc_feature
<222> LOCATION: (30)..(30)
<223> OTHER INFORMATION: N is nucleotide A, C, U, or G
<220> FEATURE:
<221> NAME/KEY: misc_feature
<222> LOCATION: (34)..(34)
<223> OTHER INFORMATION: N is nucleotide A, C, U, or G
<220> FEATURE:
<221> NAME/KEY: misc_feature
<222> LOCATION: (35)..(35)
<223> OTHER INFORMATION: N is nucleotide A, C, U, or G
<220> FEATURE:
<221> NAME/KEY: misc_feature
<222> LOCATION: (36)..(36)
<223> OTHER INFORMATION: N is nucleotide A, C, U, or G
<220> FEATURE:
<221> NAME/KEY: misc_feature
<222> LOCATION: (37)..(37)
<223> OTHER INFORMATION: N is nucleotide A, C, U, or G
<220> FEATURE:
<221> NAME/KEY: misc_feature
<222> LOCATION: (38)..(38)
<223> OTHER INFORMATION: N is nucleotide A, C, U, or G
<220> FEATURE:
<221> NAME/KEY: misc_feature
<222> LOCATION: (39)..(39)
<223> OTHER INFORMATION: N is nucleotide A, C, U, or G
<220> FEATURE:
<221> NAME/KEY: misc_feature
<222> LOCATION: (45)..(45)
<223> OTHER INFORMATION: N is nucleotide A, C, U, or G and may or may
      not be present
<220> FEATURE:
<221> NAME/KEY: misc_feature
<222> LOCATION: (48)..(48)
<223> OTHER INFORMATION: N is nucleotide A, C, U, or G
<220> FEATURE:
<221> NAME/KEY: misc_feature
<222> LOCATION: (55)..(55)
<223> OTHER INFORMATION: N is nucleotide A, C, U, or G and may or may
      not be present
<220> FEATURE:
<221> NAME/KEY: misc_feature
<222> LOCATION: (56)..(56)
<223> OTHER INFORMATION: N is nucleotide A, C, U, or G and may or may
      not be present
<220> FEATURE:
<221> NAME/KEY: misc_feature
<222> LOCATION: (57)..(57)
<223> OTHER INFORMATION: N is nucleotide A, C, U, or G and may or may
      not be present
<220> FEATURE:
<221> NAME/KEY: misc_feature
<222> LOCATION: (58)..(58)
<223> OTHER INFORMATION: N is nucleotide A, C, U, or G and may or may
      not be present
<220> FEATURE:
<221> NAME/KEY: misc_feature
<222> LOCATION: (59)..(59)
<223> OTHER INFORMATION: N is nucleotide A, C, U, or G and may or may
      not be present
<220> FEATURE:
<221> NAME/KEY: misc_feature
<222> LOCATION: (63)..(63)
<223> OTHER INFORMATION: N is nucleotide A, C, U, or G
<220> FEATURE:
<221> NAME/KEY: misc_feature
<222> LOCATION: (66)..(66)
<223> OTHER INFORMATION: N is nucleotide A, C, U, or G and may or may
      not be present
<220> FEATURE:
<221> NAME/KEY: misc_feature
<222> LOCATION: (67)..(67)
<223> OTHER INFORMATION: N is nucleotide A, C, U, or G and may or may
      not be present
<220> FEATURE:
<221> NAME/KEY: misc_feature
```

-continued

```
<222> LOCATION: (68)..(68)
<223> OTHER INFORMATION: N is nucleotide A, C, U, or G and may or may
      not be present
<220> FEATURE:
<221> NAME/KEY: misc_feature
<222> LOCATION: (69)..(69)
<223> OTHER INFORMATION: N is nucleotide A, C, U, or G and may or may
      not be present
<220> FEATURE:
<221> NAME/KEY: misc_feature
<222> LOCATION: (70)..(70)
<223> OTHER INFORMATION: N is nucleotide A, C, U, or G and may or may
      not be present
<220> FEATURE:
<221> NAME/KEY: misc_feature
<222> LOCATION: (71)..(71)
<223> OTHER INFORMATION: N is nucleotide A, C, U, or G and may or may
      not be present
<220> FEATURE:
<221> NAME/KEY: misc_feature
<222> LOCATION: (72)..(72)
<223> OTHER INFORMATION: N is nucleotide A, C, U, or G and may or may
      not be present
<220> FEATURE:
<221> NAME/KEY: misc_feature
<222> LOCATION: (73)..(73)
<223> OTHER INFORMATION: N is nucleotide A, C, U, or G and may or may
      not be present
<220> FEATURE:
<221> NAME/KEY: misc_feature
<222> LOCATION: (74)..(74)
<223> OTHER INFORMATION: N is nucleotide A, C, U, or G and may or may
      not be present
<220> FEATURE:
<221> NAME/KEY: misc_feature
<222> LOCATION: (75)..(75)
<223> OTHER INFORMATION: N is nucleotide A, C, U, or G and may or may
      not be present
<220> FEATURE:
<221> NAME/KEY: misc_feature
<222> LOCATION: (76)..(76)
<223> OTHER INFORMATION: N is nucleotide A, C, U, or G and may or may
      not be present
<220> FEATURE:
<221> NAME/KEY: misc_feature
<222> LOCATION: (77)..(77)
<223> OTHER INFORMATION: N is nucleotide A, C, U, or G and may or may
      not be present
<220> FEATURE:
<221> NAME/KEY: misc_feature
<222> LOCATION: (78)..(78)
<223> OTHER INFORMATION: N is nucleotide A, C, U, or G and may or may
      not be present
<220> FEATURE:
<221> NAME/KEY: misc_feature
<222> LOCATION: (85)..(85)
<223> OTHER INFORMATION: N is nucleotide A, C, U, or G and may or may
      not be present
<220> FEATURE:
<221> NAME/KEY: misc_feature
<222> LOCATION: (86)..(86)
<223> OTHER INFORMATION: N is nucleotide A, C, U, or G and may or may
      not be present
<220> FEATURE:
<221> NAME/KEY: misc_feature
<222> LOCATION: (87)..(87)
<223> OTHER INFORMATION: N is nucleotide A, C, U, or G and may or may
      not be present
<220> FEATURE:
<221> NAME/KEY: misc_feature
<222> LOCATION: (88)..(88)
<223> OTHER INFORMATION: N is nucleotide A, C, U, or G and may or may
      not be present
<220> FEATURE:
<221> NAME/KEY: misc_feature
<222> LOCATION: (89)..(89)
<223> OTHER INFORMATION: N is nucleotide A, C, U, or G and may or may
      not be present
<220> FEATURE:
```

```
<221> NAME/KEY: misc_feature
<222> LOCATION: (90)..(90)
<223> OTHER INFORMATION: N is nucleotide A, C, U, or G and may or may
      not be present
<220> FEATURE:
<221> NAME/KEY: misc_feature
<222> LOCATION: (91)..(91)
<223> OTHER INFORMATION: N is nucleotide A, C, U, or G and may or may
      not be present
<220> FEATURE:
<221> NAME/KEY: misc_feature
<222> LOCATION: (92)..(92)
<223> OTHER INFORMATION: N is nucleotide A, C, U, or G and may or may
      not be present
<220> FEATURE:
<221> NAME/KEY: misc_feature
<222> LOCATION: (93)..(93)
<223> OTHER INFORMATION: N is nucleotide A, C, U, or G and may or may
      not be present
<220> FEATURE:
<221> NAME/KEY: misc_feature
<222> LOCATION: (94)..(94)
<223> OTHER INFORMATION: N is nucleotide A, C, U, or G and may or may
      not be present
<220> FEATURE:
<221> NAME/KEY: misc_feature
<222> LOCATION: (95)..(95)
<223> OTHER INFORMATION: N is nucleotide A, C, U, or G and may or may
      not be present
<220> FEATURE:
<221> NAME/KEY: misc_feature
<222> LOCATION: (96)..(96)
<223> OTHER INFORMATION: N is nucleotide A, C, U, or G and may or may
      not be present
<220> FEATURE:
<221> NAME/KEY: misc_feature
<222> LOCATION: (97)..(97)
<223> OTHER INFORMATION: N is nucleotide A, C, U, or G and may or may
      not be present
<220> FEATURE:
<221> NAME/KEY: misc_feature
<222> LOCATION: (98)..(98)
<223> OTHER INFORMATION: N is nucleotide A, C, U, or G and may or may
      not be present
<220> FEATURE:
<221> NAME/KEY: misc_feature
<222> LOCATION: (99)..(99)
<223> OTHER INFORMATION: N is nucleotide A, C, U, or G and may or may
      not be present
<220> FEATURE:
<221> NAME/KEY: misc_feature
<222> LOCATION: (100)..(100)
<223> OTHER INFORMATION: N is nucleotide A, C, U, or G and may or may
      not be present

<400> SEQUENCE: 2
ggaaaaunnn nnunauaugn nnnncunnn uuunnnnnna aaaanuanaa acaunnnnnc          60
uunagnnnnn nnnnnnnag aaaunnnnnn nnnnnnnnnn uuagcag                      107

<210> SEQ ID NO 3
<211> LENGTH: 163
<212> TYPE: RNA
<213> ORGANISM: Unknown
<220> FEATURE:
<221> NAME/KEY: misc_feature
<222> LOCATION: ()..()
<223> OTHER INFORMATION: snRNA

<400> SEQUENCE: 3
aaaaaaaagg uuucaugcg ugcucacaga ucagcucuuu cuggauugaa aagcuaagca         60
cagaacaugg gaaaauuccu uucauauggc uguguuuaca aacaaaaagu auaaacaucu       120
ugagcaaaca gaaaugguga ggaaaacuuu guuagcagau uag                        163
```

```
<210> SEQ ID NO 4
<211> LENGTH: 298
<212> TYPE: RNA
<213> ORGANISM: Unknown
<220> FEATURE:
<221> NAME/KEY: misc_feature
<222> LOCATION: ()..()
<223> OTHER INFORMATION: snRNA

<400> SEQUENCE: 4
uuacagcucu ucuguuuaua aguuauucaa uaccaaauua guaguuugua uguuauaaau        60
uuguaggaaa auaauuauau augcuuacuu uguacauaaa aauaaaaaca ugacuucuuu       120
agacacuccu ucauuagaaa uaaaauaaaa uaaacuauua gcaguuugac uucauguucu       180
gucuguaggu cauggaaucc uguccuuaca auauuuauug auugugaaaa uaucaguaaa       240
uaagcaauug aauauguuua ccuuuucuuc uagucacuau guucuuagag uuaugaca        298
```